United States Patent [19]

Dahlen et al.

[11] 4,187,558
[45] Feb. 12, 1980

[54] PROSTHETIC LIGAMENT

[75] Inventors: Burton L. Dahlen, Cardiff-by-the-Sea; James A. Stubstad, Lafayette, both of Calif.

[73] Assignee: Cutter Laboratories, Inc., Berkeley, Calif.

[21] Appl. No.: 844,678

[22] Filed: Oct. 25, 1977

[51] Int. Cl.² .............................................. A61F 1/24
[52] U.S. Cl. .................................... 3/1; 128/92 C
[58] Field of Search ................. 3/1, 1.9, 1.91, 1.911, 3/1.912, 1.913; 128/92 C

[56] References Cited

U.S. PATENT DOCUMENTS

| | | | |
|---|---|---|---|
| 3,683,422 | 8/1972 | Stemmer et al. | 3/1.9 X |
| 3,745,590 | 7/1973 | Stubstad | 3/1.9 |
| 3,805,300 | 4/1974 | Tascon-Alonso et al. | 3/1 |
| 3,953,896 | 5/1976 | Treace | 3/1 |
| 3,973,277 | 8/1976 | Semple et al. | 3/1 |

Primary Examiner—Clifford D. Crowder
Attorney, Agent, or Firm—James A. Giblin; Bertram Bradley; Robert E. Allen

[57] ABSTRACT

Surgically implantable skeletal ligament having secured thereto at least one deformable collar having a velour-like outer surface adapted to invite tissue ingrowth. In use, the collar portion of the ligament is positioned within a surgically prepared passageway in a bone to protect the ligament from bone abrasion and to assist in ligament attachment by accepting tissue ingrowth into the velour-like surface.

9 Claims, 6 Drawing Figures

PROSTHETIC LIGAMENT

BACKGROUND OF THE INVENTION

1. Field

This disclosure is concerned generally with prosthetic devices and specifically with an artificial skeletal ligament.

2. Prior Art

A ligament is a tough band of tissue serving to connect the articular extremities of bones or to support an organ in place. Since skeletal ligaments flexibly stabilize joints, they must withstand considerable amounts of force. Frequently, the skeletal ligaments are subjected to enough force to be torn or otherwise damaged, thereby resulting in instability of the joint. This results in pain and possible damage to other tissues. Although some torn ligaments can be repaired by simply sewing the torn ends together, such repair is not always possible in cases of severe damage or disease. Further, surgical repair is not always predictable and requires a healing period of minimal stress before the ligament can be functionally useful.

The above circumstances have led to the development of a variety of artificial ligaments. Examples of such ligaments can be seen in U.S. Pat. No. 3,988,783 (Collateral Ligament) and U.S. Pat. No. 3,953,896 (Cruciate Ligament), both issued to Treace. Other examples of related prostheses include U.S. Pat. No. 3,973,277 (Bone Implant) to Semple et al, U.S. Pat. No. 3,805,300 (Tendon Prosthesis) to Tascon-Alonso et al, U.S. Pat. No. 3,613,120 (Tendon) to McFarland, U.S. Pat. No. 3,545,008 (Tendon) to Bader, and U.S. Pat. No. 3,842,441 (Tendon Implant) to Kaiser.

Although prosthetic ligaments have a variety of outward appearances, they commonly consist of a flexible longitudinal material having two end portions. The end portions are used to firmly attach the ligament to two adjoining bones such as, for example, the lower femur and the upper tibia. In use, the flexible central portion of the prosthetic ligament is subjected to repeated flexing, stress, and, in some cases, abrasion against bone edges. This can result in deterioration and possible rupture of the prosthesis. Although it has been disclosed that damage due to bone abrasion can be minimized or eliminated by passing the ligament through a flared stainless steel bushing-like device cemented into a bone opening (e.g. U.S. Pat. No. 3,953,896), such devices tend to serve as ligament guides rather than as means for assisting in ligament attachment. Further, the stainless steel bushings that have been disclosed are very hard and do not provide an energy sink for the stresses of a flexing ligament. Without some sort of an energy sink at the points where a flexing ligament contacts a solid body, the possibility of damage due to built up stresses within the flexing ligament is thought to be increased.

We have made a prosthetic ligament which offers advantages over existing ligaments by uniquely combining a means for enhancing ligament attachment within a bone with means for providing an energy sink to minimize the possibility of damage from repeated flexing and abrasion. Details of our findings are disclosed herein.

SUMMARY OF THE INVENTION

The ligament of this disclosure comprises an elongated, flexible, biocompatable connecting member having secured thereto at least one deformable biocompatable collar having two major surfaces, an inner surface in contact with the flexible connecting member and an outer velour-like surface adapted to invite tissue ingrowth when the collar portion of the ligament is surgically implanted within a man-made tunnel within a living bone through which the ligament is attached. In preferred embodiments, the elongate flexible connecting member comprises a longitudinally reinforced elastomer having two end portions each having associated therewith means for securing the end portion of the ligament to separate bones. In additionally preferred embodiments, two such deformable collars are attached to the connecting member, each of the collars being disposed on the connecting member near positions of intended entry into the man-made tunnels within each of the bones to be connected. In yet further preferred embodiments the two collars have outwardly flared mouth portions disposed about the ligament at intended positions of ligament entry into the respective bone tunnels, the flared portions of both such collars being directed toward a central portion of the ligament and adapted to loosely receive those portions of the ligament proceeding from the center of the ligament toward the ends.

SPECIFIC EMBODIMENTS

Figure 1:
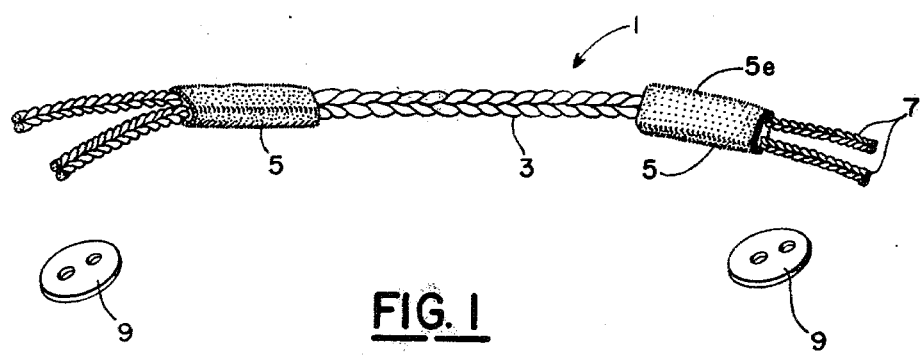
FIG. 1 illustrates one embodiment of a ligament of this disclosure.

One embodiment of the ligament of this disclosure is illustrated very generally in FIG. 1. As can be seen in FIG. 1, the ligament consists of an elongated central portion 3 having two end portions continuous therewith and terminating with two end attachments 7. In the specific illustration of FIG. 1, the end attachments 7 are adapted to pass through holes in a keeper button 9 after which the two separated end attachments of each ligament end portion can be simply tied in place (as in knot 15 of FIG. 3) to secure the end portions of the ligament in place. The specific method of anchoring or keeping the ligament end portions in place is not critical to the present invention. Other attachment modes (keeper means) are known and shown, for example, in U.S. Pat. No. 3,953,896 involving the use of nuts on threaded ligament end portions. The only requirements for the ligament end portion attachment means are that they be capable of securing the ligament firmly in a bone and that they be biocompatable. These requirements can be met, for example by using a variety of polymeric materials or with metals such as titanium alloy.

The central portion 3 of the ligament is a flexible elastomeric material which is preferably internally reinforced with, for example, a high strength braided material such as a Dacron (polyethylene terephthalate) polymer. Other reinforcing materials may be used as long as they are biocompatable, flexible, and compatable with the encasing elastomer (which is a smooth material such as silicone rubber which does not invite ingrowth).

Figure 2:
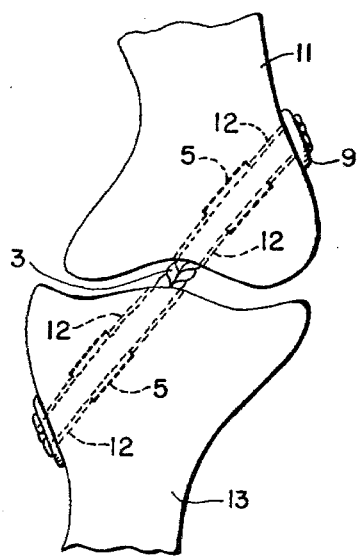
FIG. 2 is an illustration of the ligament of FIG. 1 in place connecting two skeletal members.
Figure 3:
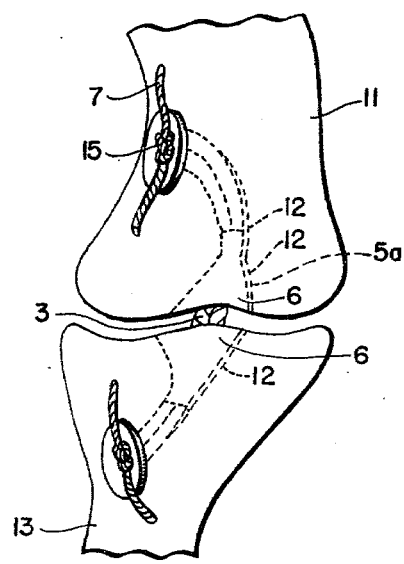
FIG. 3 illustrates the ligament of FIG. 4 in place connecting two skeletal members.

Attached to the ligament 1 of FIG. 1 are two collars 5 the use of at least one of which is an essential feature of the present disclosure. The collars each have velour-like outer surfaces, having associated therewith numerous minute projections or knitted loops 5e which provide a basis for tissue ingrowth when the ligament is in place, as illustrated in FIGS. 2 and 3. As used herein, the expression velour-like, when used with reference to the outer surface of the collars (i.e. the surface facing the walls of the bone tunnels into which they are inserted) includes any surface bearing numerous projections or pores which, when in contact with living tissue, invite or facilitate tissue ingrowth and, hence, ligament attachment in addition to the keeper means. The requirement of tissue ingrowth surfaces on the collars is important because tissue ingrowth increases the ligament attachment with time. In the case of known attachment means (buttons, nuts, etc.), however, which are commonly made of stiff unnatural prosthetic materials, there is a tendency to loosen with time due to high local stresses which may produce bone resorption (shrinking away).

As can be seen in FIGS. 2 and 3, both of which illustrate the replacement of a cruciate ligament connecting the adjacent portions of a femur 11 and a tibia 13, the ligament can be drawn through surgically prepared tunnels 12 drilled through each bone. Preferably, the tunnels are just wide enough to admit the collars 5 snugly when drawn therethrough with, for example, a lead wire (not shown). In both FIGS. 2 and 3 the end attachments of the ligaments are shown secured with the two-holed buttons 9 illustrated in FIG. 1. In practical embodiments, the end attachments 7 are trimmed to prevent significant projection beyond the outer surface of the bones, thereby avoiding tissue abrasion problems. It should be stressed, however, that other attachment means are known and may be used.

FIG. 3 illustrates the use of an especially preferred embodiment of the ligament collars. In that figure, the flared collars 5a are positioned at the bone tunnel apertures which are opposite one another and each flared collar 5a has a flared mouth portion 6 where the flexible central portion 3 of the ligament enters the bone. In one embodiment, the largest diameter of the flared portion 6 of the collar 5a is at least about 1.4 times the diameter of the ligament portion passing therethrough. Such a flared configuration is preferred because it, in combination with deformation properties, avoids ligament abrasion by bone edges at the entrance site.

Although the ligament of FIG. 1 (non-flared collars) has been used with success in short term tests, (see the article by R. L. Leighton et al, "Experimental and Clinical Evaluation of a New Prosthetic Anterior Cruciate Ligament in the Dog", JAAHA, Vol. 12, pp. 735–740, November/December, 1976), for longer terms the use of ligaments having flared collars is preferred. The use of a flared deformable collar for the ligaments is based on two well proven engineering principles. The first principle states that a relatively soft, deformable jacket around a stiffer structural object increases the lifetime of the composite by serving as an energy sink during deformation and as an abrasion buffer. Two common examples of this principle are the thin rubber threads on high pressure "sew-up" bicycle tires which help absorb road shocks and protect the cord from abrasion (as well as to increase traction) and the rubber or plastic coating on high quality garden hoses which allows them to be dragged over sidewalks and driveways a limited number of times without abrading the internal cord. The cord serves to resist air pressure (tire) or water pressure (hose) and acts as the main structural member.

The second principle states that bending stresses may be reduced by increasing radii of curvature in lines or cables. The windlass used on old sailing ships to haul in anchor lines needed a large diameter so the line would not be broken due to stress concentrations at the point of contact between line and machine.

The flared modification is shown in detail in FIG. 4, described below. Unlike the collars 5 of FIG. 1 which are placed within the bony condyles, the flared collars 5a extend slightly within the joint space and isolate the prosthesis core from bone. The taper of the collar allows for a gradual bend in the reinforcing cord as it enters the joint space and decreases stress concentration which occur in the first design due to the sharp bend as the prosthesis exits the condyles. Preferably, the flare or taper is at least about 10 degrees relative to plane of the attached collar walls and the flared portion extends for a distance of at least about 20% the length of the collar.

Figure 5:
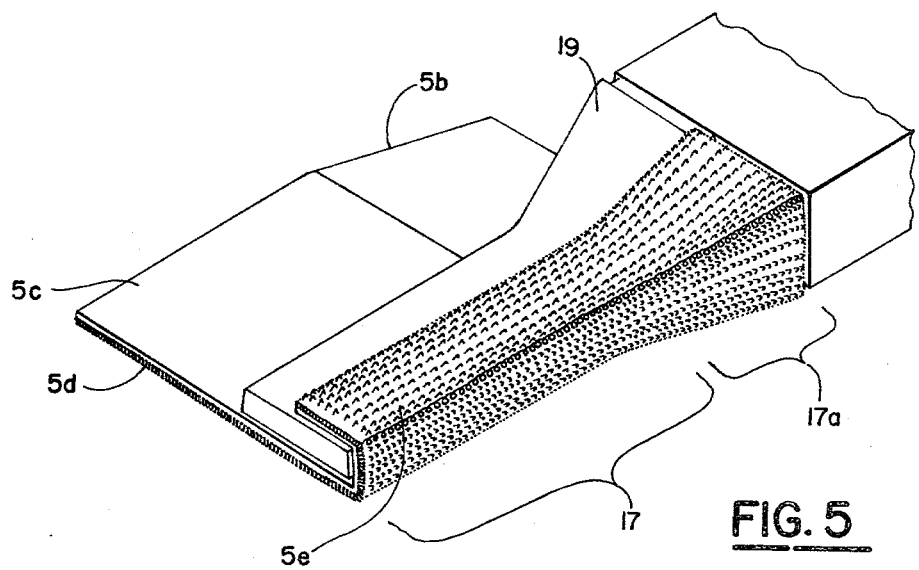
FIG. 5 illustrates a method of making the collar portions of FIG. 4.
Figure 6:
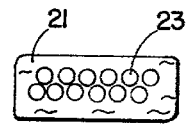
FIG. 6 represents a cross sectional view of the center of a preferred ligament, the section being taken through line 6—6 in FIG. 4.

It should be noted that regardless of the configuration of the collar, it must be made of a deformable material which is relatively softer than the central ligament portion passing therethrough. As noted above, this requirement of having a relatively softer collar, which deforms during ligament flexing, around a relatively stiffer elongated portion increases the overall composite lifetime. As also indicated above, the deformable collar also serves as an abrasion buffer. FIGS. 4, 5, and 6 illustrate a very preferred embodiment of a cruciate ligament of the type illustrated generally in FIG. 3. FIG. 4 shows a prosthetic ligament adapted to be surgically implanted and adapted to be held in place by passing the respective ends 7 through surgically drilled tunnels or passageways which are wide enough to snugly accept the two collars 5a. After exiting from the tunnels, the ligament ends can be secured to the respective bones by known means such as via the use of the buttons as described above.

The presently preferred ligament consists of a flexible core 23, which may be treated for better adhesion, comprising reinforcing braided strands of Dacron fiber 7a which have been braided from sub-strand fibers 7b. The braided multifiliment flexible core 23 is encased in an elastomeric material 21 such as a silicone polymer which has been vulcanized around the central braided portion by known means. Secured to the ligament of FIG. 4 are two flared collars 5a having a velour-like outer surface shown as 5e in FIGS. 1 and 5. The flared collars 5a can be fabricated in a variety of ways such as by simply wrapping a laminated sheet like structure 5b consisting of a Dacron velour fabric 5d bonded to a silicone rubber sheet 5c around an appropriate mandrel 19 adapted to allow formation of a flared portion length 17a approximately 0.7 times the length of the unflared portion length 17 of the collar. The unflared portion length 17 is of a size such that it fits snugly within the bone tunnel which can also be tapered at the orifice. The laminated sheet like structure 5b from which the flared collar is made can be simply stitched together with mandrel stitches 27 after fitting on the mandrel 19. The formed collars 5a can then be slipped over the ligament ends and stitched into place by stitches 25 into the flexible core 23 up to the flared portion. In one embodiment the collars are further secured or bonded to the ligament by subjecting the attached collars to a vulcanization step to bond the inner silicone surface 5c to the Dacron braid already in intimate contact therewith. This step may be done when the silicone elastomer 21 is bonded about the centrally located Dacron braids 23.

In one embodiment, the collars having the velour-like surface are made as follows: a thin sheet of a suitable biocompatable fabric having a velour-like surface (e.g. a Dacron velour having a thickness of 0.010 to 0.020 inch) is laid over and in contact with a sheet of an unvulcanized biocompatable elastomer such as silicone rubber about 0.005 to 0.040 inch in thickness. Then, pressure of about 10,000 to 20,000 psi is applied to the sheets under conditions (e.g. about 1 min. at room temperature) to result in penetration of the silicone rubber into the fabric. The unvulcanized sheet is then placed over a mandrel and trimmed. This is followed by vulcanizing and curing by known means. The actual sizes and location on the ligament of the collar members will vary depending on intended use. For example, in the manufacture of canine cruciate ligaments according to this disclosure, three sizes (large, medium and small) may be made wherein the collars (at nearest points of ligament attachment) are spaced from one another at distances of about 1.2, 0.8, and 0.4 inches.

Figure 4:
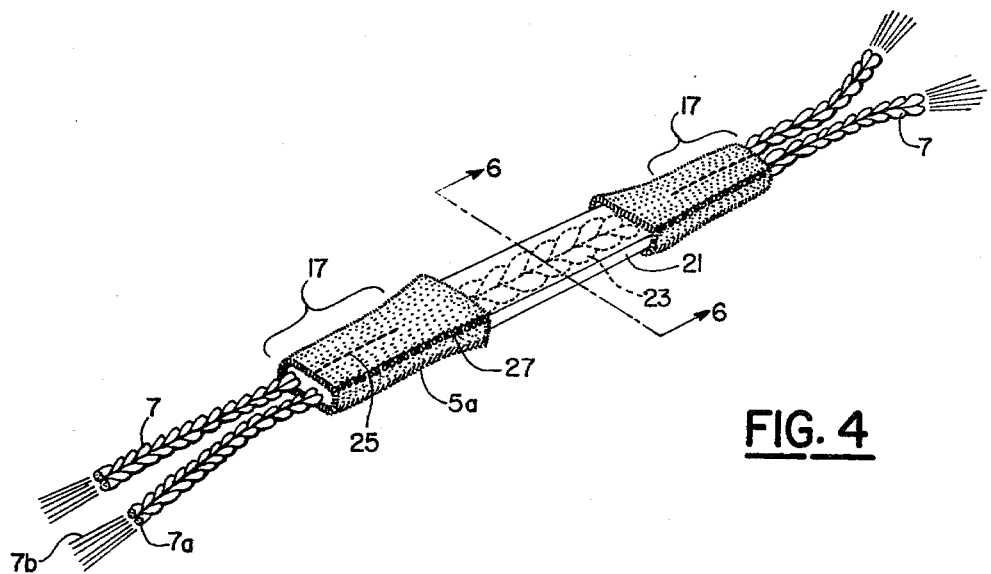
FIG. 4 illustrates a preferred ligament of this disclosure.

FIG. 6 illustrates a cross-sectional view of the flexible central portion of the ligament taken along lines 6—6 in FIG. 4. As can be seen the central portion consists of Dacron braid members 23 encased within a elastomeric casing 21 such as a silicone rubber. Other elastomeric materials may be used as long as they are biocompatable, flexible, and do not invite tissue ingrowth since the portion of the ligament between the collars, flared or not flared, must be free to flex and move among surrounding tissues as the connected bones are moved relative to one another.

An experimental prosthetic anterior cruciate ligament made in accordance with this disclosure has been clinically evaluated in dogs. The results and further details concerning the uses of that ligament are described in the above-cited article by R. L. Leighton et al. Although the ligament disclosed herein is especially adapted to serve as a cruciate ligament, it can be appreciated that this disclosure has application in any situation where a prosthetic ligament can be used to join two skeletal members in dogs and other living animals such as man.

Given the disclosures of the above described ligaments, it is thought that numerous variations within the spirit of our invention will occur to others. Accordingly it is intended that the specific examples described above should be construed as illustrative only and that the scope of the invention should be limited only by the following claims.

We claim:

1. A surgically implantable skeletal ligament comprising an elongated flexible body having two end portions and having secured thereto between the end portions at least one collar member, the collar member being a deformable material having two major surfaces, an inner surface in intimate contact with the ligament body and an opposite outer velour-like surface adapted to invite tissue ingrowth when the collar of the ligament is implanted within a living bone, the collar member including a deformable flared mouth portion continuous with and extending from the collar member and adapted to loosely receive a portion of the ligament body prior to its intimate contact with and attachment to the collar member.

2. The ligament, as claimed in claim 1, wherein the collar member comprises a laminate material having a first layer of a polymeric fabric of knitted fibers of polyethylene terephthalate bonded to a second layer of an elastomeric material.

3. In a prosthetic ligament used to flexibly connect first and second skeletal members and comprising an elongated flexible body having two end portions, one end portion adapted for attachment to the first skeletal member and the other end portion adapted for attachment to the second skeletal member, the improvement which comprises having at least one collar member positioned around and attached to the ligament body at a position intermediate the end portions, the collar comprising a deformable material having two major surfaces, an inner surface in contact with the ligament body and an opposite outer velour-like surface adapted to invite tissue ingrowth when the collar of the ligament is placed within a bone of a living animal, the collar member including a flared mouth portion continuous with and extending from the collar member, the flared mouth portion adapted to loosely receive a portion of the ligament body prior to its contact with and attachment to the collar member.

4. The ligament, as claimed in claim 3, wherein the collar member comprises a laminate material having a first layer of a fabric of knitted fibers of polyethylene terephthalate bonded to a second layer of an elastomeric material.

5. The ligament, as claimed in claim 4, wherein the layer of elastomeric material is comprised of a silicone rubber.

6. In a prosthetic ligament used to flexibly connect first and second skeletal members in a living animal and comprising an elongated flexible body having two end portions, a first end portion having means associated therewith for ligament attachment to the first skeletal member and a second end portion having means associated therewith for ligament attachement to the second skeletal member, the improvement which comprises having first and second collar members attached to the ligament body between the first and second end portion attachment means, the two collar members being separated from one another by a central portion of the ligament body and positioned on said body at positions on the ligament adapted to permit surgical implantation of the first collar member within the first skeletal member and surgical implantation of the second collar member within the second skeletal member, each collar member having two major surfaces, one surface in intimate contact with the ligament body and the other opposite velour-like surface adapted to invite and receive tissue ingrowth when the collars are implanted within the skeletal members, thereby enhancing ligament attachment with time.

7. The ligament, as claimed in claim 6, wherein the collar members include flared mouth portions continuous with and attached to the collar members, the flared mouth portions each being deformable, directed toward the central portion of the ligament body, the mouth portions being adapted to loosely receive portions of the ligament body prior to their contact with and attachment to the collar members, the collars being positioned on the ligament body at positions of intended ligament entry into drilled passageways in the first and second skeletal members such that when in place within each skeletal member, the widest portion of each flared mouth is positioned in each skeletal member at about the skeletal surface.

8. The ligament, as claimed in claim 7, wherein, the collars comprise a laminate material comprising an outer first layer of polymeric fabric having velour-like surfaces bonded to an inner layer of an elastomeric material.

9. The ligament, as claimed in claim 8 wherein the inner elastomeric material comprises a silicone rubber and the outer fabric comprises knitted fibers of polyethylene terephthalate.

* * * * *